(12) United States Patent
Kakuta et al.

(10) Patent No.: US 11,919,850 B2
(45) Date of Patent: Mar. 5, 2024

(54) BIFUNCTIONAL (METH)ACRYLATE COMPOUND AND POLYMER

(71) Applicant: Maruzen Petrochemical Co., Ltd., Chuo-ku (JP)

(72) Inventors: Satoshi Kakuta, Chiba (JP); Hiromitsu Baba, Ichihara (JP); Teruyo Ikeda, Ichihara (JP); Ryo Fujisawa, Narashino (JP); Kazuhiko Haba, Chiba (JP)

(73) Assignee: Maruzen Petrochemical Co., Ltd., Chuo-ku (JP)

( * ) Notice: Subject to any disclaimer, the term of this patent is extended or adjusted under 35 U.S.C. 154(b) by 836 days.

(21) Appl. No.: 16/971,043

(22) PCT Filed: Feb. 20, 2019

(86) PCT No.: PCT/JP2019/006341
§ 371 (c)(1),
(2) Date: Aug. 19, 2020

(87) PCT Pub. No.: WO2019/171958
PCT Pub. Date: Sep. 12, 2019

(65) Prior Publication Data
US 2020/0392066 A1    Dec. 17, 2020

(30) Foreign Application Priority Data

Mar. 7, 2018   (JP) .................. 2018-040907

(51) Int. Cl.
| | |
|---|---|
| C08F 283/01 | (2006.01) |
| C07C 69/013 | (2006.01) |
| C07C 69/608 | (2006.01) |
| C08F 22/10 | (2006.01) |
| C08F 122/10 | (2006.01) |
| C08F 222/10 | (2006.01) |
| C08F 290/08 | (2006.01) |
| C08L 33/14 | (2006.01) |
| G03F 7/004 | (2006.01) |
| C08F 2/48 | (2006.01) |

(52) U.S. Cl.
CPC .......... *C07C 69/608* (2013.01); *C07C 69/013* (2013.01); *C08F 22/10* (2013.01); *C08F 122/10* (2013.01); *C08F 222/10* (2013.01); *C08F 222/102* (2020.02); *C08F 283/01* (2013.01); *C08F 290/08* (2013.01); *C08L 33/14* (2013.01); *G03F 7/004* (2013.01); *C08F 2/48* (2013.01)

(58) Field of Classification Search
None
See application file for complete search history.

(56) References Cited

U.S. PATENT DOCUMENTS

| | | |
|---|---|---|
| 2010/0110362 A1 | 5/2010 | Parri et al. |
| 2016/0363860 A1 | 12/2016 | Hirayama et al. |

FOREIGN PATENT DOCUMENTS

| | | |
|---|---|---|
| JP | 62-53664 A | 3/1987 |
| JP | 2002-148816 A | 5/2002 |
| JP | 2002-338627 A | 11/2002 |
| JP | 2005-283632 A | 10/2005 |
| JP | 2010-522893 A | 7/2010 |
| JP | 2014-81633 A | 5/2014 |
| JP | 2017-3920 A | 1/2017 |
| WO | WO 2008/119427 A1 | 10/2008 |
| WO | WO 2013/141265 A1 | 9/2013 |
| WO | 2017-226616 A | 12/2017 |
| WO | WO 2017/209161 A1 | 12/2017 |

OTHER PUBLICATIONS

Extended European Search Report dated Oct. 26, 2021 in European Patent Application No. 19764523.7, 6 pages.
International Search Report dated Mar. 26, 2019 in PCT/JP2019/006341 filed on Feb. 20, 2019, 2 pages.

*Primary Examiner* — David J Buttner
(74) *Attorney, Agent, or Firm* — Oblon, McClelland, Maier & Neustadt, L.L.P.

(57) ABSTRACT

Provided is a compound that can be used for a resin for a resist having excellent sensitivity, resolution, and etching resistance, or the like, by a compound represented by the following formula (1):

(wherein $R_1$ represents a hydrogen atom or a methyl group, $R_2$ represents an aliphatic hydrocarbon group having 1 to 6 carbon atoms, m represents an integer of 0 to 5, and n represents an integer of 0 to 4).

2 Claims, No Drawings

BIFUNCTIONAL (METH)ACRYLATE COMPOUND AND POLYMER

TECHNICAL FIELD

The present invention relates to a new bifunctional (meth)acrylate compound useful for producing a resin for semiconductor lithography represented by a resist, an adhesive, a glue, an ink, a paint, a film, or the like, a polymer thereof, a resin composition for a resist containing the polymer thereof, a curable composition containing the bifunctional (meth)acrylate compound, and a cured product thereof.

BACKGROUND ART

In lithography, with an increase in the degree of integration, the formation of a finer pattern is demanded, and at present, a lithography technique using a KrF excimer laser beam (wavelength: 248 nm) or an ArF excimer laser beam (wavelength: 193 nm) is used in mass production. Further, it is said that microfabrication at a level of about 50 nm or less is possible by combining an excimer laser and an immersion lithography technique. In addition, research and development are progressing also on a lithography technique using an F2 excimer laser beam with a shorter wavelength (wavelength: 157 nm), or an EUV (extreme ultraviolet beam), an X-ray, or an electron beam with a shorter wavelength than that of such an excimer laser.

One of such high-resolution lithography materials is a chemically amplified resist. A polymer to serve as a base material of the chemically amplified resist contains a constituent unit having a structure in which a polar group is protected by an acid-dissociable group that can be detached by the action of an acid, and in an exposed portion, the acid-dissociable group is detached by the action of an acid generated from a photoacid generator so that the polarity of the polymer is changed to cause a difference in solubility in a developer between an exposed portion and an unexposed portion, and thus, a pattern can be formed.

As a monomer used in the synthesis of a polymer for such a chemically amplified resist, a compound having a structure in which a hydroxy group of hydroxystyrene is protected by an acid-dissociable group, or a compound having a structure in which a carboxy group of acrylic acid or methacrylic acid (hereinafter referred to as (meth)acrylic acid) is protected by an acid-dissociable group is used. In particular, in lithography using an ArF excimer laser, an acid-dissociable (meth)acrylate ester having favorable transmittance at a wavelength of 193 nm is preferably used.

PTL 1 indicates that by using a polyfunctional (meth)acrylate ester in which a hydrogen atom of a carboxyl group is substituted with an acid-dissociable crosslinking group as a comonomer, a crosslinked structure is introduced into a polymer, which is advantageous to the improvement of developing contrast and etching resistance. However, what is illustrated in PTL 1 is only a di- or tri-ester of a chain diol or triol such as 2,5-dimethylhexanediol diacrylate, and a new monomer that provides a resin for a resist having further excellent sensitivity, resolution, and etching resistance has been demanded.

CITATION LIST

Patent Literature

PTL 1: JP-A-2002-148816

SUMMARY OF INVENTION

Technical Problem

An object of the present invention is to provide a polymer for a resist that has excellent sensitivity, resolution, and etching resistance, and a new monomer compound that provides the polymer.

Solution to Problem

As a result of intensive studies for achieving the above object, the present inventors found that a compound having a specific structure can achieve the object, and thus completed the present invention.

That is, the present invention is directed to a compound represented by the following formula (1):

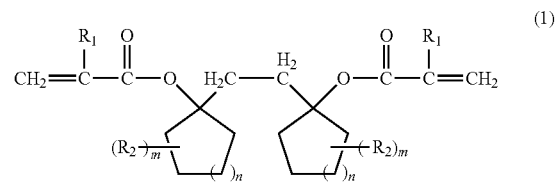

(wherein $R_1$ represents a hydrogen atom or a methyl group, $R_2$ represents an aliphatic hydrocarbon group having 1 to 6 carbon atoms, m represents an integer of 0 to 5, and n represents an integer of 0 to 4).

Further, the present invention is directed to a polymer using the above compound as a monomer, and a resin composition for a resist containing the polymer.

In addition, the present invention is directed to a curable composition containing the above compound, and a cured product thereof.

Still further, the present invention is directed to a crosslinking agent containing the above compound, a curable resin composition characterized by containing the crosslinking agent and a resin having an ethylenic double bond in the structure, and a cured product obtained by curing the curable resin composition.

Advantageous Effects of Invention

By the polymer using a (meth)acrylate ester of the present invention, a resin for a resist having excellent sensitivity, resolution, and etching resistance can be provided.

DESCRIPTION OF EMBODIMENTS

The compound of the present invention is a compound represented by the following formula (1).

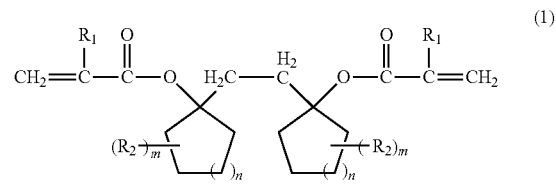

Here, in the formula (1), $R_1$ represents a hydrogen atom or a methyl group. $R_2$ represents an aliphatic hydrocarbon group having 1 to 6 carbon atoms, preferably a methyl group, an ethyl group, an isopropyl group, or a t-butyl group. m represents an integer of 0 to 5, preferably an integer of 0 to 2. n represents an integer of 0 to 4, preferably an integer of 1 to 3.

Specific examples of the compound represented by the formula (1) include 1,2-bis-[(1-acryloyloxy)cyclooxetanyl] ethane, 1,2-bis-[(1-acryloyloxy)cyclopentyl]ethane, 1,2-bis-[(1-acryloyloxy)cyclohexyl]ethane, 1,2-bis-[(1-acryloyloxy)cycloheptyl]ethane, 1,2-bis-[(1-acryloyloxy) cyclooctyl]ethane, 1,2-bis-[(1-methacryloyloxy) cyclooxetanyl]ethane, 1,2-bis-[(1-methacryloyloxy) cyclopentyl]ethane, 1,2-bis-[(1-methacryloyloxy) cyclohexyl]ethane, 1,2-bis-[(1-methacryloyloxy) cycloheptyl]ethane, 1,2-bis-[(1-methacryloyloxy) cyclooctyl]ethane, and the like.

The compound of the present invention can be produced as follows.

First, a cyclic ketone compound represented by the following formula (2) is reacted with acetylene in the presence of a solvent and an alkali catalyst.

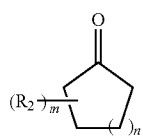

(2)

Here, the definitions and preferred embodiments of $R_2$, m, and n in the formula (2) are the same as those in the formula (1).

The alkali catalyst used in the above reaction is not particularly limited, but can be selected from alkali metals such as metallic sodium and metallic potassium; alkali metal hydroxides such as sodium hydroxide, potassium hydroxide, and lithium hydroxide; or alkali metal alcoholates such as potassium methylate, potassium ethylate, potassium isobutyrate, potassium t-butoxide, sodium methylate, and sodium ethylate. Among these, an alkali metal hydroxide is preferred.

The used amount of the alkali catalyst in the above reaction is not particularly limited, but is 0.1 to 20 mol, preferably 0.5 to 10 mol with respect to 1 mol of the ketone of the formula (2).

The solvent used in the above reaction is not particularly limited, and a saturated aliphatic hydrocarbon, an aromatic hydrocarbon, an aliphatic ether, or an aprotic polar solvent can be used. Among these, a saturated aliphatic hydrocarbon is preferred, and examples thereof include hexane, heptane, octane, nonane, decane, cyclopentane, cyclohexane, methylcyclopentane, methylcyclohexane, decalin, and the like. Among these, hexane, cyclohexane, methylcyclopentane, and methylcyclohexane are particularly preferred.

The used amount of the solvent in the above reaction is not particularly limited, but is 2 to 20 times, preferably 2 to 10 times the weight of the ketone of the formula (2).

In the above reaction, specifically, an alkali metal compound, an aliphatic hydrocarbon solvent, and a cyclic ketone compound represented by the formula (2) are placed in a pressure resistant reaction vessel made of stainless steel or the like, the inside of the pressure resistant reaction vessel is replaced with nitrogen gas, and then, the reaction vessel is closed tightly, and while introducing acetylene by applying pressure, acetylene is reacted with the cyclic ketone compound represented by the formula (2) by raising the temperature. The reaction temperature is not particularly limited, but is 0 to 100° C., preferably 10 to 60° C. The reaction pressure is not particularly limited, but is generally 0 to 1 MPa (gauge pressure), preferably 0 to 0.2 MPa (gauge pressure) as an acetylene partial pressure. The higher the acetylene partial pressure is, the higher the reaction rate is. However, acetylene tends to cause explosive decomposition, and therefore, in order to prevent it, it is preferred to decrease the acetylene partial pressure as much as possible. Incidentally, in order to prevent explosive decomposition, acetylene may be diluted by introducing an inert gas such as nitrogen, argon, or propane and then allowed to react. The reaction time depends on the other conditions such as a reaction temperature and an acetylene partial pressure, but in the case of a batch system, it is generally 0.5 to 20 hours, preferably 1 to 8 hours. Note that the reaction may be terminated when the absorption of acetylene becomes zero.

After the above reaction, a washing treatment, an extraction treatment, a purification treatment, and a drying treatment may be carried out as needed.

By the above reaction, a diol compound represented by the following formula (3) is obtained.

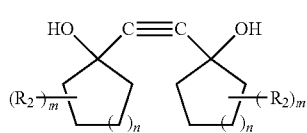

(3)

Here, the definitions and preferred embodiments of $R_2$, m, and n in the formula (3) are the same as those in the formula (1).

Subsequently, the compound represented by the formula (3) is hydrogenated.

The hydrogenation reaction is not particularly limited, but is carried out, for example, by bringing the compound of the formula (3) and hydrogen into contact with each other using a solvent such as a saturated aliphatic hydrocarbon, an aromatic hydrocarbon, an aliphatic alcohol, or an aliphatic ether in the presence of a hydrogenation catalyst.

The hydrogenation catalyst used in the hydrogenation reaction is not particularly limited, and for example, a metal catalyst such as nickel, palladium, ruthenium, rhodium, or platinum is used, and such a metal catalyst is generally used as a metal-supported hydrogenation catalyst in which the metal catalyst is supported on a carrier such as carbon, silica, alumina, silica alumina, or magnesia. Examples of the metal-supported hydrogenation catalyst include Pd/C and the like. The supported amount of the metal is not particularly limited, but is preferably 0.3 to 10 wt %. Further, as such a metal-supported hydrogenation catalyst, a commercially available catalyst can be used.

The used amount of the metal catalyst in the hydrogenation reaction is not particularly limited, but is, for example, in the range of 0.001 to 1 wt %, preferably 0.05 to 0.5 wt % in terms of the metal amount with respect to the compound of the formula (3).

The conditions for the hydrogenation reaction are not particularly limited. The hydrogenation reaction can also be carried out in a reaction vessel made of glass. In such a case, the hydrogen pressure may be around normal pressure and also the temperature may be around room temperature. If hydrogen is introduced using a gas burette in the hydrogenation reaction, the consumption amount of hydrogen can be quantitatively determined. The reaction time of the hydrogenation reaction is not particularly limited, but is, for example, 1 to 20 hours, preferably 2 to 10 hours. Further, when a pressure resistant vessel is used in the hydrogenation, the hydrogen pressure is 0.3 to 15 MPa, preferably 0.5 to 10 MPa, the reaction temperature is 10 to 150° C., preferably 20 to 100° C., and the reaction time is 1 to 20 hours, preferably 2 to 10 hours.

After the above reaction, a washing treatment, an extraction treatment, a purification treatment, and a drying treatment may be carried out as needed.

By the above reaction, a diol compound represented by formula (4) is obtained.

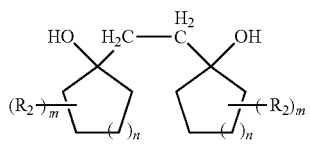

(4)

Here, preferred embodiments of $R_2$, m, and n in the formula (4) are the same as those in the formula (1).

Subsequently, the diol compound represented by the formula (4) is converted to a (meth)acrylate ester. The conversion of the diol compound represented by the formula (4) to a (meth)acrylate ester can be carried out by a known method, and examples thereof include a normal esterification reaction in which a diol and (meth)acrylic acid are reacted in the presence of an acid catalyst, a transesterification reaction using another (meth)acrylate ester, a method in which the diol compound is reacted with anhydrous (meth)acrylic acid, a method in which a (meth)acrylic acid halide is allowed to react in the presence of an organic base, and the like.

The (meth)acrylic acid halide used in the above reaction is not particularly limited, but examples thereof include acrylic acid chloride, acrylic acid bromide, methacrylic acid chloride, methacrylic acid bromide, and the like.

The amount of the (meth)acrylic acid halide in the above reaction is not particularly limited, but is 1.0 to 10 times equivalent, preferably 1.2 to 5 times equivalent to the amount of the diol compound represented by the formula (4).

The organic base used in the above reaction is preferably an organic amine, and examples thereof include aliphatic amines such as methylamine, dimethylamine, trimethylamine, ethylamine, diethylamine, triethylamine, n-propylamine, di-n-propylamine, diisopropylamine, tri-n-propylamine, n-butylamine, di-n-butylamine, and diisobutylamine; aromatic amines such as aniline, methylaniline, and toluidine; and heterocyclic amines such as pyridine, pyrrole, and piperidine.

The amount of the organic base in the above reaction is not particularly limited, but is 1.0 to 10 times equivalent, preferably 1.2 to 5 times equivalent to the amount of the (meth)acrylic acid halide.

A solvent used in the above reaction is not particularly limited. As the solvent, for example, an aromatic hydrocarbon solvent such as toluene or xylene, an aliphatic hydrocarbon solvent such as hexane or heptane, an ether-based solvent such as diethyl ether, tetrahydrofuran, monoethylene glycol dimethyl ether, or diethylene glycol dimethyl ether, a ketone-based solvent such as acetone, methyl ethyl ketone, or methyl isobutyl ketone, a nitrile solvent such as acetonitrile or benzonitrile, an ester-based solvent such as ethyl acetate, butyl acetate, or γ-butyrolactone, an amide-based solvent such as dimethylformamide, dimethylacetamide, or N-methylpyrrolidone, or the like can be used.

The reaction temperature in the above reaction is not particularly limited, but is −20 to 80° C., preferably −10° C. to 30° C.

After the above reaction, a washing treatment, an extraction treatment, a purification treatment, and a drying treatment may be carried out as needed.

By the production method described above, the compound represented by the formula (1) of the present invention is obtained. Whether or not the compound is produced can be confirmed by a known method such as NMR.

The compound represented by the formula (1) of the present invention is reacted with itself or with a monomer copolymerizable with the compound represented by the formula (1), whereby a polymer having a constituent unit derived from the compound can be obtained. Examples of such a monomer include a monomer having an ethylenic double bond, and the structure thereof is not particularly limited, but examples thereof include a styrene-type monomer, a (meth)acrylate-type monomer, a norbornene-type monomer, and the like. The styrene-type monomer is a monomer having a skeleton similar to that of styrene, and examples thereof can include styrene, vinylnaphthalene, vinylanthracene, hydroxystyrene, and the like, and derivatives having various substituents attached thereto. The (meth)acrylate-type monomer is a monomer having a skeleton similar to that of (meth)acrylic acid, and examples thereof can include acrylic acid, methacrylic acid, and various (meth)acrylate esters derived therefrom. The norbornene-type monomer is a monomer having a skeleton similar to that of norbornene, and examples thereof can include norbornene, tricyclodecene, tetracyclododecene, and the like, and derivatives having various substituents attached thereto. Further, indene, acenaphthylene, and the like are also copolymerizable. In addition, when the polymer of the present invention is used for resist applications, as the monomer, various monomers having an ethylenic double bond used for known resist resins can also be used for adjusting the solubility in a lithographic solvent or an alkaline developer, substrate adhesion, or the like.

As the polymerization reaction, known radical polymerization, cationic polymerization, or anionic polymerization can be adopted. The conditions for each polymerization reaction are not limited, but for example, in the case of radical polymerization, the reaction is carried out at 40 to 160° C., particularly preferably 60 to 120° C. in the presence of an azo-based polymerization initiator or a peroxide-based polymerization initiator. It is preferred to use a solvent, and the solvent is preferably selected depending on the types of the monomer, the radical polymerization initiator, and the polymer to be produced so that the solvent well dissolves these members.

The polymer can be used for the application of, for example, a resist necessary for semiconductor lithography, or the like. In particular, the polymer is preferably used for a resin composition for a resist containing the polymer. The resin composition for a resist contains, other than the polymer, an acid generator, an acid diffusion inhibitor, a solvent for forming a coating film for uniformly dissolving these members, or the like.

The acid generator is appropriately selected from those conventionally proposed as an acid generator for a chemically amplified resist and can be used. Examples thereof can include onium salts such as iodonium salts and sulfonium salts, oxime sulfonates, diazomethanes such as bisalkyl or bisarylsulfonyldiazomethanes, nitrobenzyl sulfonates, iminosulfonates, disulfones, and the like, and among these, onium salts are preferred. These may be used alone or two or more types may be used in combination. The acid generator is used in an amount ranging generally from 0.5 to 30 parts by mass, preferably from 1 to 10 parts by mass with respect to 100 parts by mass of the polymer of the present invention.

The acid diffusion inhibitor can be appropriately selected from those conventionally proposed as an acid diffusion inhibitor for a chemically amplified resist. Examples thereof can include nitrogen-containing organic compounds, and primary to tertiary alkylamines or hydroxyalkylamines are preferred. Particularly, tertiary alkylamines and tertiary hydroxyalkylamines are preferred, and above all, triethanolamine and triisopropanolamine are particularly preferred. These may be used alone or two or more types may be used in combination. The acid diffusion inhibitor is used in an amount ranging generally from 0.01 to 5.0 parts by mass with respect to 100 parts by weight of the polymer of the present invention.

The solvent for forming a coating film may be any as long as it can dissolve the respective components constituting the resin composition for a resist to forma uniform solution, and an arbitrary solvent selected from solvents known as solvents for forming a coating film can be used as a single solvent of one type or a mixed solvent of two or more types. A solvent having at least one or more types of polar groups selected from a ketone bond, an ester bond, an ether bond, and a hydroxy group has excellent solubility, and therefore is preferred. Among them, a solvent having a boiling point at normal pressure of 110 to 220° C. has a moderate evaporation rate in baking after spin coating, and has an excellent film forming property, and therefore is particularly preferred. Specific examples of such a solvent can include solvents having a ketone bond such as methyl isobutyl ketone, methyl isoamyl ketone, methyl amyl ketone, and cyclohexanone, solvents having an ether bond and a hydroxy group such as propylene glycol monomethyl ether (PGME) and propylene glycol monoethyl ether, solvents having an ether bond and an ester bond such as propylene glycol monomethyl ether acetate (PGMEA), propylene glycol monoethyl ether acetate, and ethyl 3-ethoxypropionate, solvents having an ester bond and a hydroxy group such as methyl lactate and ethyl lactate, solvents having an ester bond such as γ-butyrolactone, and the like. Among these, PGMEA, PGME, γ-butyrolactone, and ethyl lactate are preferred.

In the resin composition for a resist, further, if desired, a compound that is commonly used as an additive for a resist such as an organic carboxylic acid or a phosphorus oxoacid for the purpose of preventing deterioration of the sensitivity of an acid generator, or improving the shape of a resist pattern, the laying stability, or the like, an additional resin for improving the performance of a resist film, a surfactant for improving the coating property, a dissolution inhibitor, a plasticizer, a stabilizer, a colorant, a halation preventing agent, or a dye can be appropriately contained as needed.

Further, the compound represented by the formula (1) of the present invention can be used as a raw material of a curable composition in the same manner as an existing (meth)acrylate ester. The curable composition can contain another (meth)acrylate ester or another polymerizable compound having an ethylenic double bond, a polymerization initiator, or the like. The polymerization initiator is not particularly limited, but examples thereof include a light (or heat) radical polymerization initiator, a light (or heat) cationic polymerization initiator, a light (or heat) anionic polymerization initiator, and the like. As such polymerization initiators, commercially available polymerization initiators can be used.

Further, the compound represented by the formula (1) of the present invention has two ethylenic double bonds, and therefore can be used as a crosslinking agent.

When the compound represented by the formula (1) of the present invention is used as a crosslinking agent, a curable resin composition can be formed by incorporating the compound in combination with a resin having an ethylenic double bond in the structure such as a resin having a vinyl group or a (meth)acryloyl group in a side chain, an unsaturated polyester, or a vinyl ester resin.

The above-mentioned curable composition and curable resin composition are each formed into a cured product by curing according to a conventional method. The shape of the cured product is not particularly limited, and a film, a molded body, and the like are exemplified.

EXAMPLES

Hereinafter, the present invention will be described in detail with reference to Examples, however, the present invention is by no means limited to these Examples.

The identification of the synthesized materials in the Examples was carried out by $^1$H-NMR and $^{13}$C-NMR. Further, the purity and yield were determined by gas chromatography.

Example 1

Synthesis of 1,2-bis-[(1-methacryloyloxy)cyclohexyl]ethane (1) Synthesis of 1,2-bis[(1-hydroxy)cyclohexyl]ethyne In a 30 L autoclave, 1,599 g of potassium hydroxide, 1,401 g of cyclohexanone, and 12.0 kg of methylcyclohexane were charged. After the inside of the reaction vessel was replaced with nitrogen, nitrogen was replaced with acetylene. Thereafter, a reaction was carried out at a reaction temperature of 30° C. and an acetylene pressure (gauge pressure) of 0.04 MPa or less, and the reaction was completed in 4 hours when the absorption of acetylene became zero. In the reaction vessel, 21 kg of ion exchanged water was added and stirred for 1 hour, and the resulting solid content was separated using a pressure filter.

Subsequently, the obtained solid content was put into a 10 L glass vessel, 5 kg of ion exchanged water was added thereto, and the mixture was stirred at room temperature for 30 minutes, and then, the solid content was separated using a pressure filter. The operation was repeated until the pH of the filtrate reached 7. The obtained solid material was dried under reduced pressure at 40° C. for 29 hours. 760 g of the resulting dry solid was subjected to simple distillation under reduced pressure (2.7 kPa, 115° C., 3 hours) to remove light components such as unreacted components. The amount of the obtained heavy components (bottom residue) was 730 g, and as a result of GC analysis, the purity of 1,2-bis[(1-hydroxy)cyclohexyl]ethyne was 98.6%.

$^{13}$C-NMR (400 MHz, CD$_3$OD): σ ppm=24.5, 26.4, 41.0, 69.1, 88.8

The above reaction is as follows.

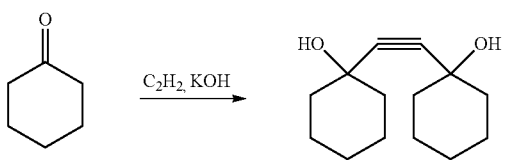 [SMILES: O=C1CCCCC1 ; OC1(C#CC2(O)CCCCC2)CCCCC1]

(2) Synthesis of
1,2-bis[(1-hydroxy)cyclohexyl]ethane
(hydrogenation)

In a 1 L four-necked flask equipped with a 500 cc gas burette (connected to a nitrogen line or a hydrogen line), a stirrer, a thermometer, and a three-way cock (connected to a vent line or a diaphragm pump), 50.0 g of 1,2-bis[(1-hydroxy)cyclohexyl]ethyne obtained in (1) and 400 g of methanol were charged, and the mixture was stirred and dissolved in a water bath at 20° C. The inside of the system including the gas burette was replaced with nitrogen by repeating decompression using the diaphragm pump, and subsequent nitrogen. Subsequently, 1.05 g of 10% Pd/C (manufactured by Wako Pure Chemical Industries, Ltd.) as a catalyst was poured into the system with 50 g of methanol. The gas connected to the gas burette was switched to a hydrogen line, and the inside of the system was replaced with hydrogen in the same manner as in the case of the nitrogen replacement. Hydrogen was charged until the scale of the water level of the gas burette showed 500 cc, and the mixture was stirred at 20 to 22° C. for 4.5 hours to carry out a hydrogenation reaction. The water level in the gas burette rose as the reaction progresses, that is, as hydrogen is consumed.

When the scale of the water level reached 0 cc, hydrogen was repeatedly charged until the scale of the water level reached 50 cc, and the hydrogen consumption was measured. The completion of the reaction was confirmed by thin-layer chromatography. The consumption amount of hydrogen was 10.6 L which was slightly larger than the theoretical amount (this is considered due to leakage of a portion outside the system). After completion of the reaction, the inside of the system was replaced with nitrogen, and thereafter, the catalyst was separated by filtration. The filtrate was concentrated to dryness at 30° C. and 2 kPa to 0.2 kPa, whereby 51.0 g of a light grayish white crude crystal was obtained.

To the crude crystal, 160 mL of tetrahydrofuran was added, and the internal temperature was raised to 47° C. to completely dissolve the crystal. Subsequently, the temperature was slowly lowered and cooled to 4° C. to sufficiently precipitate a crystal, and then, the crystal was stored overnight in a freezer at −25° C. On the following day, the crystal was separated by filtration and dried at 30° C. under reduced pressure of 0.2 kPa, whereby 44.1 g of a light grayish white crystal was obtained. The crystal was confirmed to be 1,2-bis[(1-hydroxy)cyclohexyl]ethane by NMR analysis.

$^{13}$C-NMR (400 MHz, CD$_3$OD): δ ppm=23.3, 27.1, 35.9, 38.3, 72.0

Further, as a result of GC analysis, the purity was 99.6%, and the yield was 87.4%.

The above reaction is as follows.

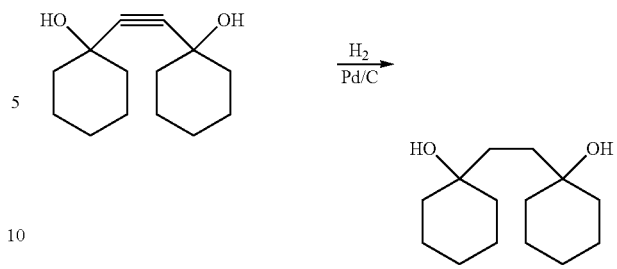

(3) Synthesis of 1,2-bis[(1-methacryloyloxy)cyclohexyl]ethane

In a 1 L four-necked flask equipped with a stirrer, a thermometer, and a dropping funnel with a side tube, 42.9 g (0.19 mol) of 1,2-bis[(1-hydroxy)cyclohexyl]ethane obtained in (2), 337 g of acetonitrile, and 69.0 g (0.68 mol) of triethylamine were charged under a pure air flow. At that time, 1,2-bis[(1-hydroxy)cyclohexyl]ethane was not dissolved. The mixture was cooled in an ice bath, and 59.4 g (0.57 mol) of methacrylic acid chloride was added dropwise thereto over 80 minutes at 10° C. or lower. After completion of the dropwise addition, the reaction was further carried out at 20° C. for 14 hours. Subsequently, the reaction solution was cooled in an ice bath, and 34.0 g of methanol was added dropwise thereto over 30 minutes at 5° C. or lower. After completion of the dropwise addition, stirring was continued at 20° C. for 3 hours.

To the reaction solution, 230.8 g of ethyl acetate and 128.7 g of ion exchanged water were added to perform a liquid-liquid extraction operation. To the aqueous layer, 115.8 g of ethyl acetate was added to further perform a liquid-liquid extraction operation. The obtained organic layers were combined, and washing was sequentially carried out with 128.7 g of 1 N hydrochloric acid, and subsequently with 132.3 g of a saturated sodium bicarbonate aqueous solution, and finally with 149 g of saturated saline. The organic layer was dehydrated with anhydrous sodium sulfate and then filtered. The filtrate was concentrated under reduced pressure at 30° C., whereby 84.2 g of a brown crude crystal was obtained. The crude crystal was dissolved in ethyl acetate, purified with a silica gel column using heptane to heptane:ethyl acetate=100:1 as an eluent, followed by concentration, whereby a yellow crystal was obtained. The yellow crystal was redissolved in 300 mL of ethyl acetate, and decolorized using 5.0 g of activated carbon. After the activated carbon was filtered, the filtrate was dried under reduced pressure, whereby 49.1 g of a slightly yellow crystal was obtained. The slightly yellow crystal was confirmed to be 1,2-bis[(1-methacryloyloxy)cyclohexyl]ethane by NMR analysis.

$^1$H-NMR (400 MHz, acetone-d6): δ ppm=1.23-1.62 (16H), 1.90 (6H), 1.94 (4H), 2.23 (4H), 5.53 (2H), 6.00 (2H)

$^{13}$C-NMR (400 MHz, acetone-d6): δ ppm=18.6, 22.6, 26.2, 31.2, 35.2, 83.9, 124.3, 139.0, 166.4

Further, as a result of GC analysis, the purity was 99.4%.

The above reaction is as follows.

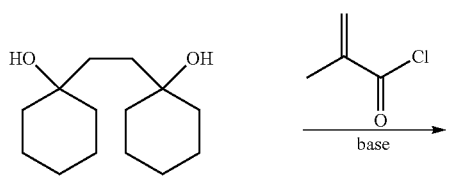

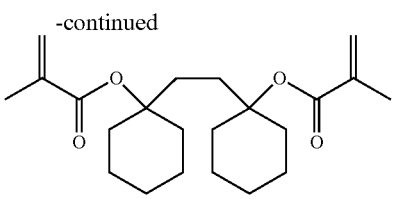

Example 2

Synthesis of γ-butyrolactone methacrylate/1-methyl-1-cyclopentyl methacrylate/1,2-bis[(1-methacryloyloxy)cyclohexyl]ethane Copolymer In a 300 mL three-necked flask equipped with a Dimroth condenser, a thermometer, and a dropping funnel, 37.3 g of methyl ethyl ketone (hereinafter MEK) was charged, and the temperature was raised to 80° C. A polymerization initiator solution in which 0.35 g of dimethyl-2,2'-azobisisobutyrate (hereinafter MAIB) was dissolved in 5 g of MEK was added dropwise thereto over 10 minutes at a constant rate, and thereafter, stirring was continued for 10 minutes. Subsequently, a monomer solution in which 3.11 g of MAIB, 24.45 g of γ-butyrolactone methacrylate, 23.87 g of 1-methyl-1-cyclopentyl methacrylate, and 5.22 g of 1,2-bis[(1-methacryloyloxy)cyclohexyl]ethane obtained in Example 1 were dissolved in 62.9 g of MEK was added dropwise thereto over 180 minutes at a constant rate, and after completion of the dropwise addition, a polymerization reaction was carried out at 80° C. for 180 minutes, and then cooled to room temperature.

150 g of the obtained polymerization solution was added dropwise to a mixed solution of 450 g of methanol and 150 g of ion exchanged water over 5 minutes, and stirring was continued for 30 minutes as it is to precipitate the resin. The operation of separating the resin by filtration under reduced pressure and washing the resin with 300 g of methanol by stirring at room temperature for 30 minutes was repeated twice. The recovered resin was dissolved in 75 g of MEK. The solution was transferred to a 1 L eggplant-shaped flask, 450 g of propylene glycol monomethyl ether acetate (hereinafter PGMEA) was added thereto, and the mixture was concentrated under reduced pressure at 40° C. until the content became 200 g, whereby a PGMEA solution of the copolymer was obtained.

The concentration of the copolymer in the obtained PGMEA solution was determined based on the heating residue, and as a result, it was 21.4 wt %. The weight average molecular weight (Mw) and molecular weight distribution (Mw/Mn) of the copolymer were determined by GPC-RI, and the monomer composition ratio was determined by $^{13}$C-NMR. The respective analysis conditions are shown below.
<Copolymer Analysis Conditions>
GPC-RI: differential refractive index detector, Shodex (registered trademark) Column LF-804×3, eluent: THF
$^{13}$C-NMR: 400 MHz, acetone-d6, Cr(III) acetylacetonate, inverse gated decoupling method The weight average molecular weight (Mw) and molecular weight distribution (Mw/Mn) of the copolymer were Mw=17,200 and Mw/Mn=3.34. Further, the monomer composition ratio of the copolymer was γ-butyrolactone methacrylate/1-methyl-1-cyclopentyl methacrylate/1,2-bis[(1-methacryloyloxy)cyclohexyl]ethane=47.8/47.7/4.5.

Example 3

Synthesis of p-hydroxystyrene/1-ethyl-1-cyclohexyl acrylate/1,2-bis[(1-methacryloyloxy)cyclohexyl]ethane Copolymer In a reaction vessel maintained in a nitrogen atmosphere, 100 g of a p-ethylphenol solution containing 25 wt % p-hydroxystyrene, 22 wt % methanol, and 10 wt % water, 9.16 g of 1-ethyl-1-cyclohexyl acrylate, 2.87 g of 1,2-bis[(1-methacryloyloxy)cyclohexyl]ethane obtained in Example 1, 0.22 g of tert-dodecyl mercaptan, and 0.90 g of MAIB were charged and dissolved. The temperature of the solution was raised from 40° C. to 80° C. at 1° C./min while stirring the solution, and a polymerization reaction was carried out at 80° C. for 2.5 hours, followed by cooling to room temperature.

The obtained polymerization solution was added dropwise to toluene to precipitate the polymer, and the supernatant was removed. Subsequently, an operation in which the precipitate is dissolved in acetone, the solution is subjected to precipitation with toluene, and the supernatant is removed was repeated twice. The precipitate was redissolved in acetone, hexane was added thereto to reprecipitate the polymer, and the supernatant was removed. The obtained precipitate was dried in a vacuum dryer, whereby a solid copolymer was obtained. The analysis of the weight average molecular weight (Mw), molecular weight distribution (Mw/Mn), and monomer composition ratio of the copolymer was carried out in the same manner as in Example 2.

The weight average molecular weight (Mw) and molecular weight distribution (Mw/Mn) of the copolymer were Mw=23,900 and Mw/Mn=7.44. Further, the monomer composition ratio of the copolymer was p-hydroxystyrene/1-ethyl-1-cyclohexyl acrylate/1,2-bis[(1-methacryloyloxy)cyclohexyl]ethane=81.3/15.5/3.2.

Example 4

Synthesis of p-hydroxystyrene/1-ethyl-1-cyclohexyl acrylate/1,2-bis[(1-methacryloyloxy)cyclohexyl]ethane Copolymer In a reaction vessel maintained in a nitrogen atmosphere, 200 g of a p-ethylphenol solution containing 25 wt % p-hydroxystyrene, 22 wt % methanol, and 10 wt % water, 16.9 g of 1-ethyl-1-cyclohexyl acrylate, 5.62 g of 1,2-bis[(1-methacryloyloxy)cyclohexyl]ethane obtained in Example 1, 0.62 g of tert-dodecyl mercaptan, and 1.94 g of MAIB were charged and dissolved. The temperature of the solution was raised from 40° C. to 80° C. at 1° C./min while stirring the solution, and a polymerization reaction was carried out at 80° C. for 2.5 hours, followed by cooling to room temperature.

The obtained polymerization solution was added dropwise to toluene to precipitate the polymer, and the supernatant was removed. Subsequently, an operation in which the precipitate is dissolved in acetone, the solution is subjected to precipitation with toluene, and the supernatant is removed was repeated twice. The precipitate was redissolved in acetone, hexane was added thereto to reprecipitate the polymer, and the supernatant was removed. The obtained precipitate was dried in a vacuum dryer, whereby a solid copolymer was obtained. The analysis of the weight average molecular weight (Mw), molecular weight distribution (Mw/Mn), and monomer composition ratio of the copolymer was carried out in the same manner as in Example 2.

The weight average molecular weight (Mw) and molecular weight distribution (Mw/Mn) of the copolymer were Mw=36,960 and Mw/Mn=3.46. Further, the monomer composition ratio of the copolymer was p-hydroxystyrene/1-ethyl-1-cyclohexyl acrylate/1,2-bis[(1-methacryloyloxy)cyclohexyl]ethane=75.8/20.4/3.8.

Comparative Example 1

Synthesis of p-hydroxystyrene/1-ethyl-1-cyclohexyl acrylate/2,5-dimethylhexyl Glycol Diacrylate Copolymer Synthesis and analysis were carried out in the same manner as in Example 4 except that 3.94 g of 2,5-dimethylhexyl glycol diacrylate was used in place of 5.62 g of 1,2-bis[(1-methacryloyloxy)cyclohexyl]ethane.

The weight average molecular weight (Mw) and molecular weight distribution (Mw/Mn) of the copolymer were Mw=33,400 and Mw/Mn=3.77. Further, the monomer composition ratio of the copolymer was p-hydroxystyrene/1-ethyl-1-cyclohexyl acrylate/2,5-dimethylhexyl glycol diacrylate=76.0/20.0/4.0.

Example 5

Preparation of Resist Composition 100 parts by mass of the copolymer synthesized in Example 4, 0.3 parts by mass of bis-(4-tert-butylphenyl) iodonium nonafluorobutanesulfonate as an acid generator, and 0.1 parts by mass of a surfactant (F447, manufactured by DIC) were dissolved in propylene glycol monomethyl ether acetate to prepare a solution having a polymer concentration of 15 wt %, and thereafter, the obtained solution was filtered through a membrane filter having a pore diameter of 0.1 μm, whereby a resist composition was obtained.

Comparative Example 2

Preparation of Resist Composition

A resist composition was obtained in the same manner as in Example 5 except that the copolymer synthesized in Comparative Example 1 was used.

Test Example 1

Evaluation of Resist Composition

The resist composition prepared in Example 5 or Comparative Example 2 was spin-coated on a silicon substrate having been subjected to a hexamethyldisilazane treatment for 1 minute on a hot plate at 100° C., and then pre-baked at 110° C. for 60 seconds on the hot plate, whereby a resist layer having a film thickness of 1.0 μm was formed.

Subsequently, by using an open frame exposure apparatus (UVES-2000, manufactured by Litho Tech Japan Corporation), 18-shot irradiation was carried out on a 10 mm×10 mm area while changing the exposure amount of light with a wavelength of 248 nm, and then, a post-baking (PEB) treatment was carried out at 120° C. for 90 seconds. Subsequently, by using a resist development rate measurement apparatus (RDA-800, manufactured by Litho Tech Japan Corporation), development was carried out with a 2.38% tetramethylammonium hydroxide aqueous solution at 23° C., and a change in the resist film thickness during development at each exposure amount was measured.

Based on the obtained data, a curve was created by plotting the relationship between the exposure amount (mJ/cm$^2$) and the ratio of the residual film thickness at the time of developing for 60 seconds to the initial film thickness (not shown). In the curve, an approximate straight line was drawn in the residual film ratio range of 10% to 70% of the residual film ratio curve, and the exposure amount (mJ/cm$^2$) when the residual film ratio reached 0% was defined as Eth sensitivity which is one of the indices of the sensitivity of the resist composition. The Eth sensitivity is an exposure amount necessary for achieving a residual film ratio of 0%, and it is indicated that as the value of the Eth sensitivity is smaller, the sensitivity of the resist composition is higher. The Eth sensitivity is shown in Table 1. Further, Rmin (that is the minimum value of the dissolution rate and corresponds to the dissolution rate in an unexposed portion) was calculated and is also shown in Table 1.

TABLE 1

| Resist composition | Eth (mJ/cm$^2$) | Rmin (nm/sec) |
|---|---|---|
| Example 5 | 8.3 | 0.02 |
| Comparative Example 2 | 7.4 | 0.22 |

The resist composition of the present invention had a substantially smaller Rmin while having equal Eth sensitivity as compared with the prior art. That is, the resist composition of the present invention reduces film reduction of an unexposed portion and can be expected to improve dissolution contrast.

Example 6

Preparation of Curable Composition and Production of Cured Product

In 50 parts by mass of tetrahydrofurfuryl acrylate as a reactive monomer, 50 parts by mass of 1,2-bis[(1-methacryloyloxy)cyclohexyl]ethane obtained in Example 1 and 5 parts by mass of a photo-radical polymerization initiator (Irgacure 379, manufactured by BASF) were mixed, whereby a curable composition was prepared.

The above curable composition was sandwiched between two PET films having been subjected to a fluorine treatment together with a spacer with a thickness of 100 μm, and the resultant was irradiated with light having a wavelength of 365 nm at 3000 mJ/cm$^2$ from a mercury lamp. Thereafter, the PET film was peeled off, whereby a film-like sample composed of a cured product of the curable resin composition was obtained.

Comparative Example 3

Preparation of Curable Composition and Production of Cured Product

A curable composition was prepared in the same manner as in Example 6 except that 2,5-dimethylhexyl glycol diacrylate (CAS No. 188837-15-2) was used in place of 1,2-bis[(1-methacryloyloxy)cyclohexyl]ethane, and a film-like sample was obtained by curing the composition.

Comparative Example 4

Preparation of Curable Composition and Production of Cured Product

A curable composition was prepared in the same manner as in Example 6 except that tricyclodecane dimethanol diacrylate (CAS No. 42594-17-2) was used in place of 1,2-bis[(1-methacryloyloxy)cyclohexyl]ethane, and a film-like sample was obtained by curing the composition.

Comparative Example 5

Preparation of Curable Composition and Production of Cured Product

A curable composition was prepared in the same manner as in Example 6 except that 9,9-bis[4-(2-acryloyloxyethoxy)phenyl]fluorene (CAS No. 1234827-45-2) was used in place of 1,2-bis[(1-methacryloyloxy)cyclohexyl]ethane, and a film-like sample was obtained by curing the composition.

Test Example 2

Evaluation of Cured Product

By using the film-like samples obtained in Example 6 and Comparative Examples 3 to 5, the dynamic viscoelasticity measurement was carried out under the following conditions to determine the glass transition point (Tg) of the cured product. The results are shown in Table 2.

<Dynamic Viscoelasticity Measurement Conditions>
Device: DMS 6100, manufactured by Seiko Instruments, Inc.
Sample piece: 1 cm×5 cm
Temperature range: 25 to 250° C.
Temperature raising rate: 2° C./min
Frequency: 1 Hz
Strain amplitude: 10 μm The cured product of Example 6 obtained by curing the curable composition using the diacrylate of the present invention has a higher Tg and therefore has excellent heat resistance as compared with the cured products of Comparative Examples 3 to 5 obtained by curing a conventional curable composition.

INDUSTRIAL APPLICABILITY

The compound represented by the formula (1) of the present invention can be used as a raw material of various curable compositions as well as a raw material for synthesis of a resin for a resist, and also as a crosslinking agent for a resin having an ethylenic double bond.

The invention claimed is:

1. A curable resin composition, comprising a crosslinking agent comprising at least one compound represented by the following formula (1); and a resin having an ethylenic double bond in the structure

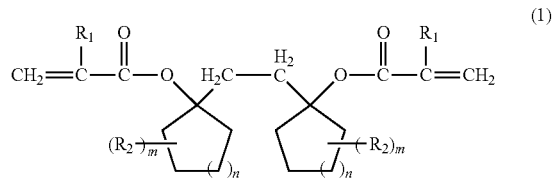

wherein $R_1$ represents a hydrogen atom or a methyl group, $R_2$ represents an aliphatic hydrocarbon group having 1 to 6 carbon atoms, m represents an integer of 0 to 5, and n represents an integer of 0 to 4.

2. A cured product, obtained by curing a composition comprising a crosslinking agent comprising at least one compound represented by the following formula (1): and a resin having an ethylenic double bond in the structure

TABLE 2

| | 50 parts by mass of reactive monomer | 50 parts by mass of di(meth)acrylate | Tg (° C.) |
|---|---|---|---|
| Example 6 | | | 96 |
| Comparative Example 3 | | | 62 |
| Comparative Example 4 | | | 69 |
| Comparative Example 5 | | | 68 |

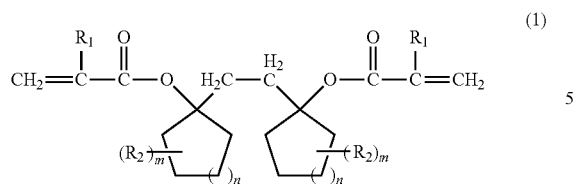 (1)
wherein $R_1$ represents a hydrogen atom or a methyl group, $R_2$, represents an aliphatic hydrocarbon group having 1 to 6 carbon atoms, m represents an integer of 0 to 5, and n represents an integer of 0 to 4.
* * * * *